(12) United States Patent
Fetzer

(10) Patent No.: US 8,486,090 B2
(45) Date of Patent: Jul. 16, 2013

(54) SURGICAL INSTRUMENT SUPPORT

(76) Inventor: Peter E. Fetzer, Oehningen-Wangen (DE)

( * ) Notice: Subject to any disclaimer, the term of this patent is extended or adjusted under 35 U.S.C. 154(b) by 790 days.

(21) Appl. No.: 11/605,744

(22) Filed: Nov. 29, 2006

(65) Prior Publication Data
US 2008/0121765 A1    May 29, 2008

(51) Int. Cl.
*A61B 19/00* (2006.01)

(52) U.S. Cl.
USPC .......................................... 606/130

(58) Field of Classification Search
USPC ................. 606/96, 99, 86 A, 130; 248/279.1, 248/160; 600/229
See application file for complete search history.

(56) References Cited

U.S. PATENT DOCUMENTS

| | | | |
|---|---|---|---|
| 5,052,373 A * | 10/1991 | Michelson | 600/217 |
| 5,320,444 A | 6/1994 | Bookwalter et al. | |
| 5,662,300 A | 9/1997 | Michelson | |
| 5,820,707 A | 10/1998 | Amick et al. | |
| 6,767,418 B1 | 7/2004 | Zhang et al. | |
| 7,182,731 B2 * | 2/2007 | Nguyen et al. | 600/229 |
| 7,195,591 B2 * | 3/2007 | Spence et al. | 600/210 |
| 7,226,409 B2 * | 6/2007 | Peng et al. | 600/37 |
| 7,241,264 B2 * | 7/2007 | Xiao et al. | 600/229 |
| 2004/0149874 A1 * | 8/2004 | Stoianovici et al. | 248/276.1 |
| 2005/0021030 A1 | 1/2005 | Pagliuca et al. | |
| 2005/0152739 A1 | 7/2005 | Ibrahim et al. | |
| 2005/0226682 A1 | 10/2005 | Chersky et al. | |

* cited by examiner

Primary Examiner — Thomas McEvoy
(74) Attorney, Agent, or Firm — McDermott Will & Emery LLP

(57) ABSTRACT

The present invention generally provides a surgical instrument support for securing a surgical instrument in a fixed position in a surgical environment having a magnetic field. The surgical instrument support has a mounting clamp, a tightening mechanism, a plurality of mating arm segments, an end member with a connector to secure the surgical instrument thereto, and a wire extending from the tightening mechanism to the end member. The wire can be tightened to secure the mating arm segments in a desired position for the surgeon. In one embodiment all of the components of the surgical instrument support are made of a non-magnetic material, preferably titanium or a titanium alloy. In another embodiment the connector of the end member can be removed when the surgical instrument support is in both the rigid or actuated configuration and the untightened or non-actuated configuration.

13 Claims, 5 Drawing Sheets

SURGICAL INSTRUMENT SUPPORT

CROSS-REFERENCE TO RELATED APPLICATIONS

Not Applicable.

FEDERALLY SPONSORED RESEARCH OR DEVELOPMENT

Not Applicable.

TECHNICAL FIELD

The present invention relates to a support for a surgical instrument, and more specifically to titanium tightening mechanisms for supporting surgical instruments within a magnetic field.

BACKGROUND OF THE INVENTION

Surgical instruments and supports for surgical instruments are well known in the art. While such surgical instrument supports according to the prior art provide a number of advantageous features, they nevertheless have certain limitations. The present invention seeks to overcome certain of these limitations and other drawbacks of the prior art, and to provide new features not heretofore available. A full discussion of the features and advantages of the present invention is deferred to the following detailed description, which proceeds with reference to the accompanying drawings.

SUMMARY OF THE INVENTION

The present invention generally provides a surgical instrument support. According to one embodiment the surgical instrument support comprises an elongated snake arm for securing surgical instruments in a fixed position in a surgical environment having a magnetic field, typically produced by an imaging machine. In this embodiment the surgical instrument support has a non-magnetic adjustable mounting clamp, a non-magnetic adjustable tightening member connected to an end of the mounting clamp, a plurality of independent non-magnetic mating hollow arm segments extending away from the mounting clamp, a non-magnetic end segment having a connector to secure the surgical instrument support to a surgical instrument and a non-magnetic wire. The wire has a first end, a second end and a middle portion therebetween. The first end of the wire is connected to the tightening member, the second end of the wire is connected to the end segment, and the middle portion extends through the hollow portions of the plurality of non-magnetic mating hollow arm segments. A portion of the tightening member is laterally moveable to tighten the wire to rigidly fix the independent arm segments and end segment in a desirable position to fix the surgical instrument in place.

According to another embodiment, the tightening member has a non-magnetic spindle and a non-magnetic crank connected to the spindle. The first end of the line is further connected to the spindle. The crank operates to manipulate the spindle to tighten the line. In another embodiment the rotatable crank transitions the spindle from an inward position to a laterally outward position to tighten the line.

According to another embodiment, the clamp has a housing with a vise. The vise is adapted to clamp onto a fixed member in the surgical environment. In one embodiment the vise is mounted adjacent a side of the mounting clamp, and in another embodiment the vise is provided in-line with the tightening member adjacent the clamp.

According to another embodiment, the arm segments have a first end, a second end, and a hollow aperture portion extending therebetween. In one embodiment the first end of the mating arm segments has a male mating geometry, and the second end of the mating arm segments has a female mating geometry. The female mating geometry of the mating arm segments is adapted to mate with the male mating geometry of an adjacent mating arm segment. According to another embodiment, the mating surfaces have different surface hardness and surface roughness to assist in preventing slipping between the components in the rigid configuration.

According to another embodiment, the surgical instrument support is made of titanium alloy components. Accordingly, the surgical instrument support comprises: a titanium alloy mounting clamp connectable to a fixed component in the surgical environment; an adjustable titanium alloy tightening mechanism adjacent the mounting clamp, the tightening mechanism having a rotatable crank and an adjustable spindle; a plurality of titanium alloy mating arm segments provided in series, the arm segments having first and second ends and an aperture extending from the first end to the second end thereof, the first end of each arm segment configured to mate with the second end of an adjacent arm segment; a titanium alloy end member having a connector adapted to secure the surgical instrument thereto; and, an elongated titanium alloy line having a first end, a second end and a middle portion therebetween, the first end being connected to the spindle, the second end being connected to the end member, and the middle portion extending through the hollow portions of the plurality of hollow arm segments, wherein the spindle is adjustable to tighten the line to shorten the distance of the line between the end member and the mounting clamp to rigidly connect the mounting clamp, independent arm segments and end segment in a fixed desirable position.

According to another embodiment, the titanium alloy of the clamp and arm segments comprises titanium, zirconium and nobium, generally with additional components.

According to another embodiment, the line that connects the arm segments and which is used to rigidly connect the mounting clamp, arm segments and end segment in the fixed desirable position comprises a titanium alloy stranded wire.

According to another embodiment, the mounting clamp has a plurality of teeth that engage the housing to secure the mounting clamp in a variety of positions.

According to another embodiment, the surgical instrument support comprises an end arm member adjacent a last of the mating arm segments, the end arm member comprising a retainer having a bore to removably secure the line therein, and a collar having central bore to seat the retainer therein and a second end configured to mate with the first end of the last of the mating arm segments. Additionally, the end arm member comprises a connector member removably secured to the collar of the end arm member. The connector has a securing member to removably connect a surgical instrument to the surgical instrument support. In a preferred embodiment the connector member can be removed from the end arm member without the line releasing the arm segments and without the line having to be moved to the non-actuated or loose condition.

According to another embodiment, the collar has a first mating member and the connector has a second mating member that matingly engages the first mating member on the collar to removably secure the connector to the collar. In one embodiment the first mating member of the collar comprises a threaded member, and the second mating member of the connector comprises another threaded member.

According to another embodiment, the collar has a stepped bore to assist in removably seating the retaining in the collar.

According to yet another embodiment, the retainer has a longitudinal slot in a sidewall thereof to receive the line therethrough.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which.

DETAILED DESCRIPTION

Figure 1:
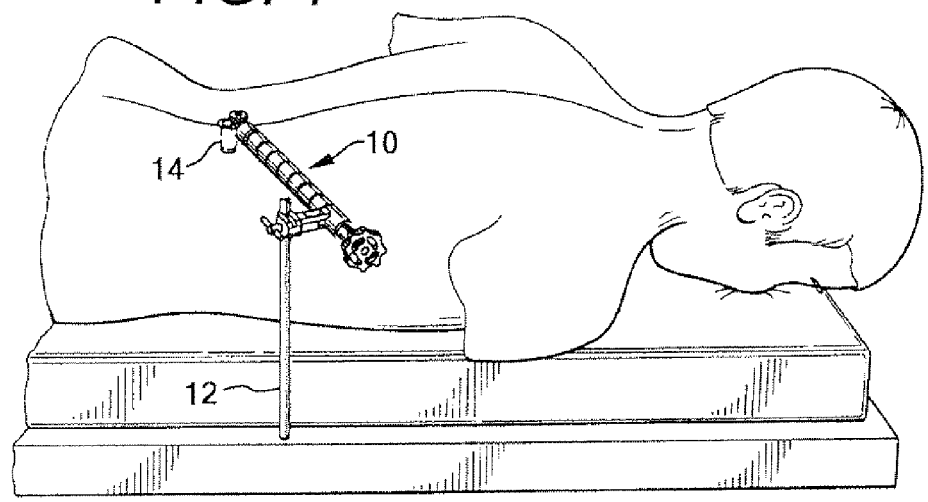
FIG. 1 is a perspective view of one embodiment of a surgical instrument support in use.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Figure 2:
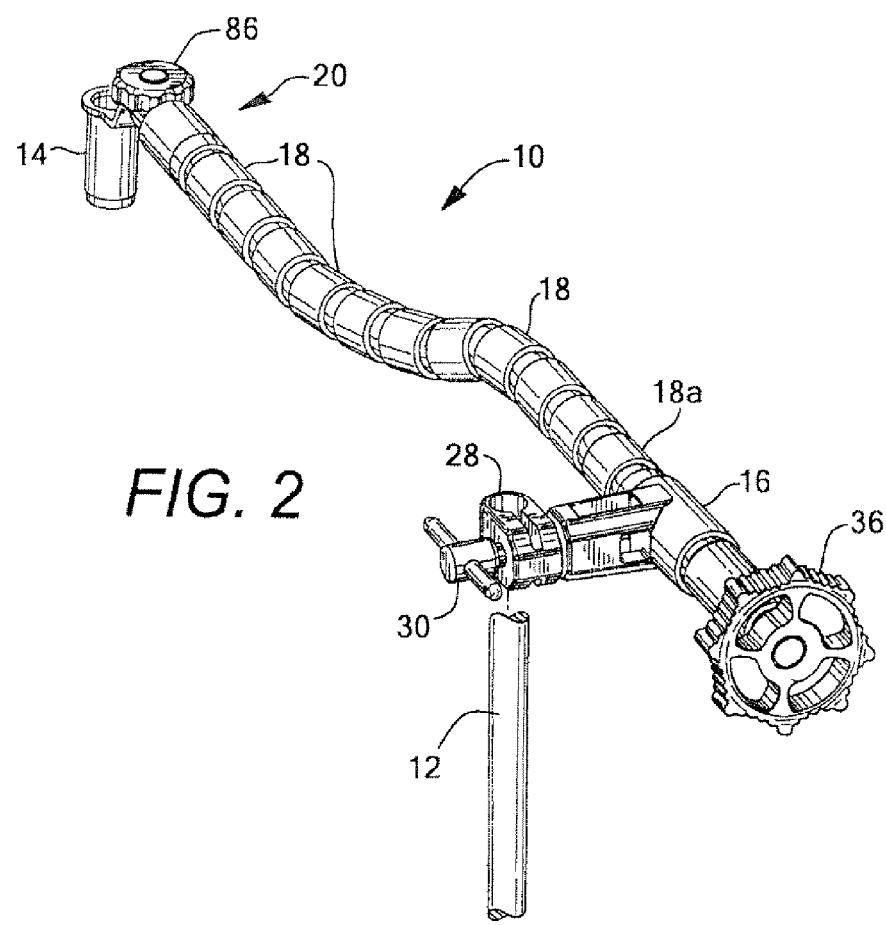
FIG. 2 is a perspective view of the surgical instrument support in the non-actuated position.
Figure 3:
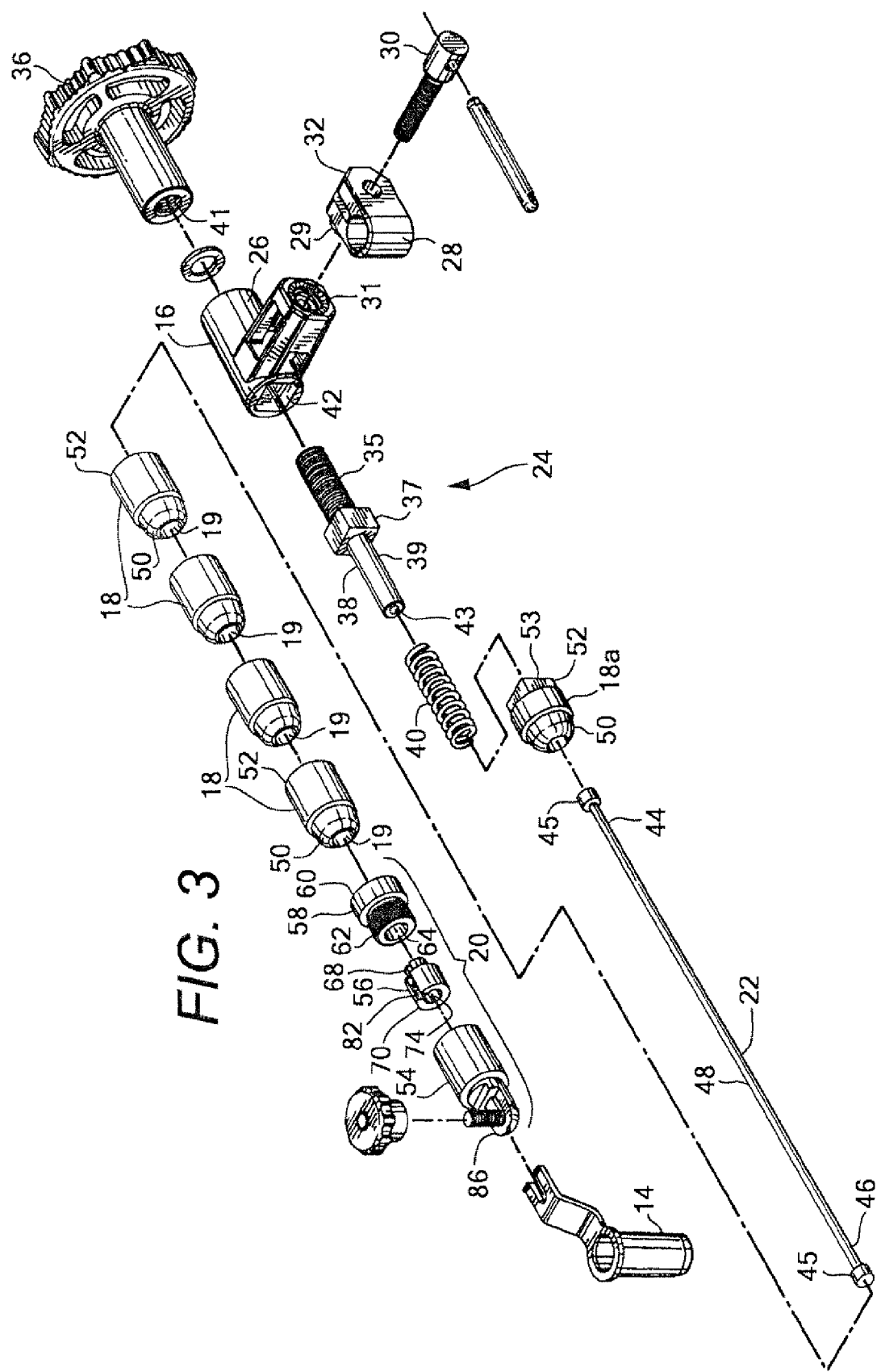
FIG. 3 is an exploded perspective view of the surgical instrument support of FIG. 2.

Referring now to the Figures, and specifically to FIGS. 1-3, there is shown a surgical instrument support 10 in the actuated or use position (FIG. 1), and the normal or non-use position (FIGS. 2 and 3). As shown in FIG. 1, the surgical instrument support 10 is a component that is supported on one end to a fixed member 12, such as a post extending from a surgical table 12, and is cantilevered outward from the fixed member 12 to fix a surgical instrument 14, connected to the distal end of the surgical instrument support 10, in a position desired by the surgeon.

In one embodiment the surgical instrument support 10 is made entirely of a non-ferrous material, preferably titanium or a titanium alloy, to allow the surgical instrument support 10 to be utilized in the presence of electromagnetic waves and electromagnetic fields, such as are present with magnetic resonance imaging (MRI) and computerized axial tomography (CAT) scan machines. MRI machines produce large electromagnetic fields, i.e., 0.5 to 2.0 tesla, and thus ferrous surgical components cannot presently be utilized real-time during surgical procedures because standard surgical instruments that are made of stainless steel or other components with certain levels of ferrite are attracted by the magnetic field in the MRI machine. The strong attraction to the magnetic field tends to move all metal instruments and metal components to the center of the magnet of the MRI machine, rendering the procedure both useless and potentially dangerous to the patient and others in the presence of the magnetic field. In another embodiment, however, where electromagnetic fields are not at issue, the surgical instrument support 10 may be made of any acceptable material, and preferably a metal material such as stainless steel or aluminum.

As shown in the Figures, the surgical instrument support 10 generally comprises a mounting clamp 16, a plurality of hollow arm segments 18, an instrument attachment end arm segment 20, a wire 22, and a tightening mechanism 24. The mounting clamp 16 is generally connected to the fixed component 12 in the surgical room, which is typically a portion of the surgical table or a post extending from the surgical table. Following the mounting of the mounting clamp 16 to the fixed component 12, the end arm segment 20 is fixed to the surgical instrument 14 and the surgical instrument 14 is positioned in the appropriate location. After the mounting clamp 16 and end arm segment 20 with surgical instrument 14 attached thereto are positioned in their appropriate respective locations, the tightening mechanism 24 is actuated to fixedly secure the end arm segment 20 in that desired position. It is understood that the arm segments may be positioned in any linear or curvilinear configuration, in the actuated or use position, that could be desired by the surgeon.

In one embodiment, the mounting clamp 16 generally has a housing or frame 26 supporting a vise or clamp 28 to assist the mounting clamp 16 in being secured to the fixed component 12 in the surgical room. The housing 26 of the mounting clamp 16 also generally supports the tightening mechanism 24 for tightening the wire 22 to fix the end arm segment 20 after the surgical instrument 14 is connected to the end arm segment 20 and the surgical instrument 14 is positioned in the proper location. In the embodiment of FIGS. 2 and 3, the mounting clamp 16 has a secondary squeezable vise or clamp 28 extending from the side of the housing 26. In this embodiment the secondary vise 28 is rotatable with respect to the housing 26, and the secondary vise 28 has a plurality of teeth 29 on a side thereof that are designed to engage mating teeth 31 on the housing 26 in a variety of angular positions to assist in securing the surgical instrument support 10 to the fixed component 12 in a desired angular position. In this embodiment a threaded spindle 30 extends through a portion of the jaws 32 of the vise 28 to open and close the clamp jaws 32 to thereby allow for securing and removing of the clamp 16 to the fixed component 12 in the surgical room.

Figure 5:
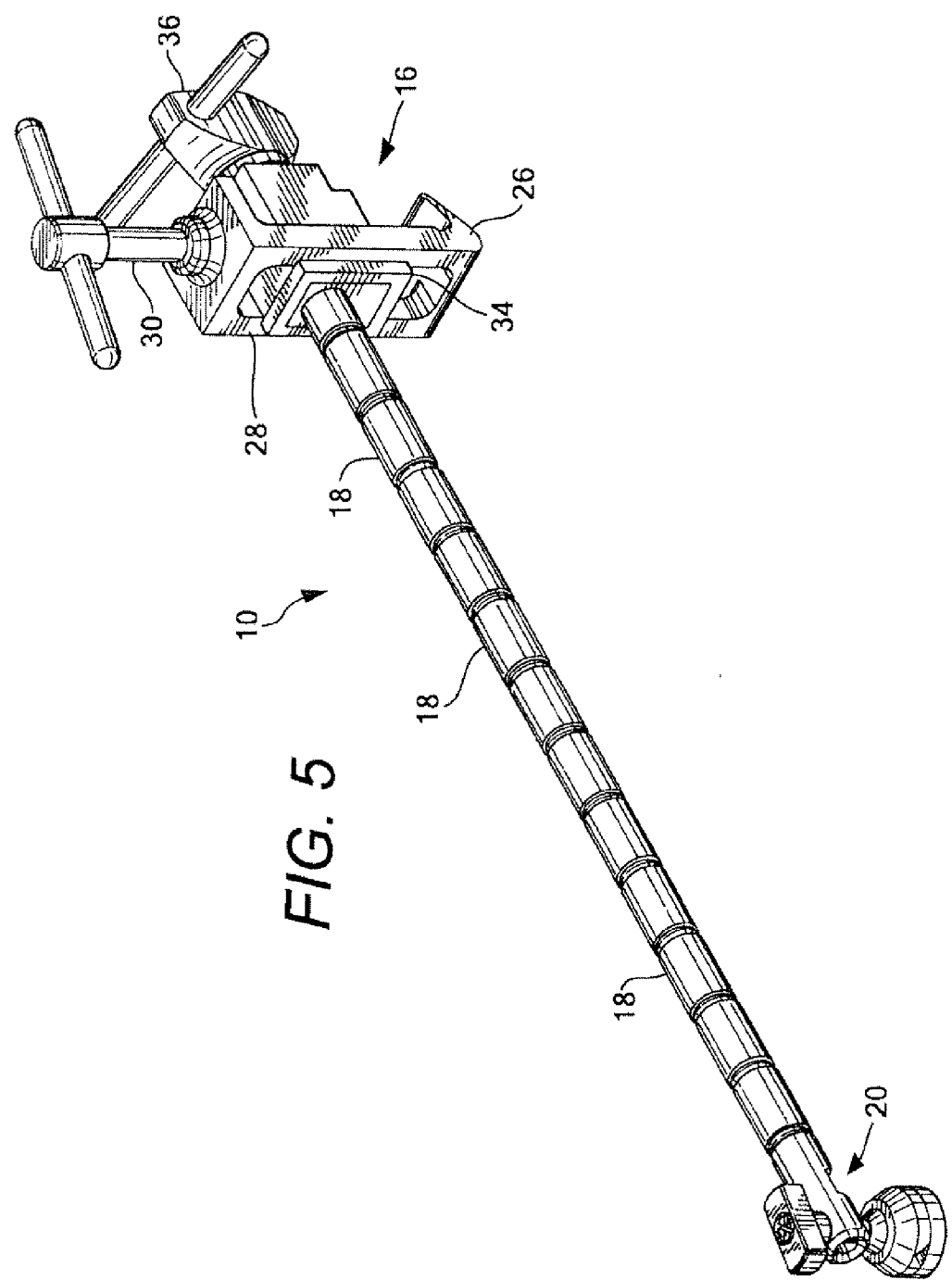
FIG. 5 is a perspective view of another embodiment of a surgical instrument support in the non-actuated position; and, FIG. 6 is an exploded perspective view of the surgical instrument support of FIG. 5.
Figure 6:
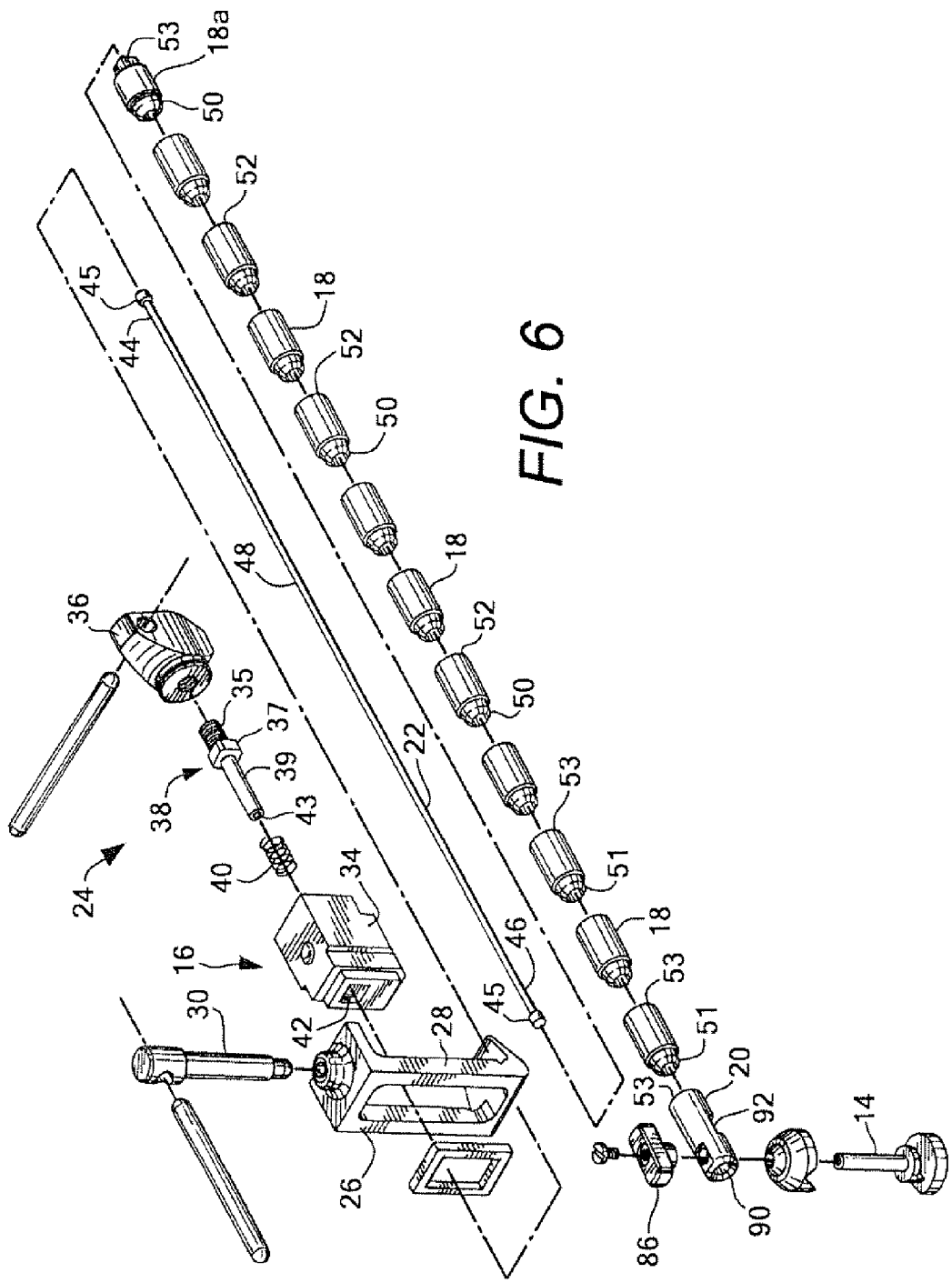

In the embodiment of FIGS. 5 and 6, the mounting clamp 16 also has a vise 28 connected to its frame 26. The vise 28 includes a moveable jaw 34 which moves in one direction as the tightening spindle 30 is rotated clockwise, and in an opposing direction as the tightening spindle 30 is rotated counterclockwise. By moving the jaw 34 the space between the jaw 34 and the frame 26 is altered, i.e., made smaller to tighten the jaw 34 against the fixed component 12 in the surgical room or made larger to loosen the jaw 34 to remove the mounting clamp 16.

Each of the mounting clamps 16 of the various embodiments of the surgical instrument support 10 preferably also have a tightening mechanism 24 supported thereon. The tightening mechanism 24 may include, but is not limited inclusively or exclusively, a rotatable crank 36 and a spindle 38. A tensioning spring 40 may also be provided to assist in maintaining tension between the arm segments during loosening of the surgical instrument support 10 such that the surgical instrument support 10, and specifically the arm segments on the wire 22, remain connected together.

The crank 36 is utilized to move the spindle 38 inward and outward with respect to the housing 26, to thereby tighten the surgical instrument support 10 when the spindle 38 is drawn inwardly, and loosen the surgical instrument support 10 when the spindle 38 is released and moved back outwardly toward the arm segments 18. In a preferred embodiment the spindle 38 has a threaded portion 35, a geometric portion 37, and a shaft portion 39. Referring to FIG. 3, in one embodiment the mating geometric portion 37 of the spindle 38 has a square shape thereto, however, one of ordinary skill in the art would readily understand that other geometries may be utilized without departing from the scope of the present invention. Similarly, the crank 36 has a bore 41 with female internal threads that are manufactured to engage and mate with the external threads on the threaded portion 35 of the spindle 38. And, the housing 26 of the mounting clamp 16 has a bore 42 that is shaped to matingly receive the geometric portion 37 of the spindle 38. Accordingly, in one embodiment the bore 42 has a square shape to mate with the square shape of the mating geometric portion 37 of the spindle 38. Further, in a preferred embodiment the second end 52 of the first arm segment 18a also has a geometric outer portion 53 which mates with the bore 42 of the mounting clamp 16 to allow the entrance of the bore 42 to receive the second end 52 of the first arm segment 18.

Typically, a portion of the spindle 38 is connected to the crank 36 to rotate with the crank 36 to move the spindle 38 inwardly and outwardly with respect to the mounting clamp 16. In a preferred embodiment the threaded portion 35 of the spindle 38 mates with and engages the threaded bore 41 in the crank 36. Accordingly, as the crank 36 is rotated in a first direction the threads on the threaded portion 35 of the spindle 38 mate and are drawn laterally inward toward the threads in the bore 41 of the crank 36, thereby tending to tighten the wire 22 and ultimately tighten the links 18 of the surgical instrument support 10 in a fixed position in place against one another. Conversely, as the crank 36 is rotated in a second opposite direction the threads of the threaded portion 35 of the spindle 38 is pushed laterally outwardly of the threads in the bore 41 of the crank 36, thereby tending to loosen the wire 22 and ultimately loosen the connection between each of the links 18 of the surgical instrument support 10. In different embodiment the tightening mechanism 24 operates differently.

In a preferred embodiment with the mating relationships as defined above, the spindle 38 does not rotate, but rather moves laterally inwardly and outwardly because the geometric portion 37 of the spindle 38 which mates with the bore 42 of the housing 26 prevents the spindle 38 from rotating. Instead, the geometric portion 37 of the spindle 38 remains in a fixed angular position, and therefore as the crank 36 rotates the threads in the bore 41 of the crank 36 adjust the lateral position of the spindle 38 to tighten or slacken the wire 22.

In a preferred embodiment the spring 40 may be provided as a portion of the tightening mechanism 24 and on the spindle 38 to assist in forcing the first arm segment 18 away from the clamp frame 26 to provide a dual benefit: first the spring 40 maintains a constant tension on the wire 22 to preclude the wire 22 from accidentally becoming separated from the end arm segment 20 at one end and the spindle 38 at the opposing end; second the tension force provided by the spring 40 assists in forcing the spindle 39 laterally away from the crank 36 during the loosing operation of the tightening mechanism 24 (i.e., when the tightening mechanism 24 is actuated from the tightened position toward the normal or non-tightened position). The spring 40 is preferably seated around the shaft portion 39 of the spindle 38. One end of the spring 40 is positioned against the mating geometric portion 37 of the spindle 38 and the other end of the spring 40 is positioned against the second end 52 of the first arm segment 18.

Referring to FIGS. 3 and 6, the wire 22 has a first end 44, a second end 46 and a middle portion 48 therebetween. The first end 44 of the wire 22 is preferably moveably connected to the spindle 38. Accordingly, in one embodiment as the spindle 38 moves laterally inwardly and outwardly the wire 22 will correspondingly move laterally with the spindle 38. More specifically, in a preferred embodiment the spindle 38 has a central bore 43 through which the wire 22 traverses. The second end 46 of the wire 22 is moveably connected to the end of the surgical instrument support 10, preferably at the end arm segment 20. Finally, the middle portion of the wire 48 extends within the hollow portions 19 of the central arm segments 18 and the spindle 38.

In a preferred embodiment, the first and second ends 44, 46 of the wire 22 have enlarged portions 45 to allow the enlarged portions 45 of the wire 22 to be secured against a shoulder within the respective spindle 38 and the instrument attachment end arm segment 20. Accordingly, the wire 22 does not rotate with any portion of the surgical instrument support 10, but instead has a connection that allows the any portion of the surgical instrument support to rotate and move the wire 22 laterally without spinning the wire 22. While the wire 22 is shown as a single wire, it is understood that a strand or cable may be utilized without departing from the scope of the present invention. Strands are produced by twisting a number of wires together, and cables are produced by stranding several strands of wire together. Strands and cables are preferred when increased strength and flexibility are needed over a single wire filament can provide.

Figure 4:
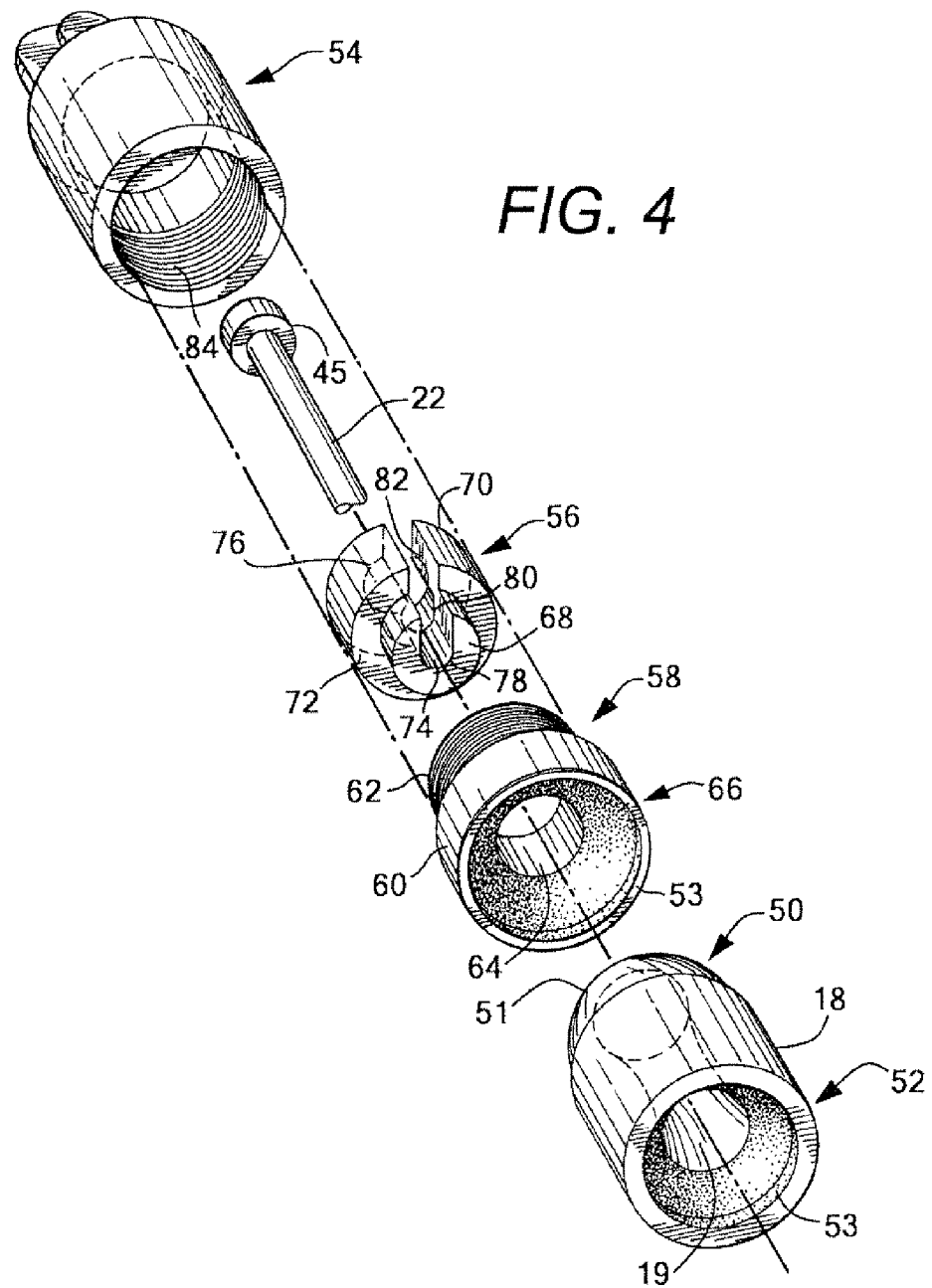
FIG. 4 is an exploded perspective view of the end connector of one embodiment of the surgical instrument support.

As best shown in FIGS. 4 and 6, in one embodiment the arm segments 18 have a bore or hollow portion 19 therethrough in which the wire 22 traverses. Preferably, the arm segments 18 are independent components that are provided in series extending along the wire 22 from the mounting clamp 16 to the end arm segment 20. In preferred embodiments each of the arm segments 18 has a first end 50 and a second end 52, and the first end 50 of each trailing arm segment 18 is configured to mate with the second end 52 of the adjacent leading arm segment 18. Most preferably, as shown in the figures, the first end 50 of the arm segments 18 has a male mating portion and the second end 52 of the arm segments 18 has a mating female mating portion to allow the adjacent arm segments 18 to mate when the tightening mechanism 24 is transitioned to the actuated position. In one embodiment the first end 50 of the arm segments 18 has a spherical or semi-spherical configuration 51, and the second end 52 of the arm segments 18 has a mating configuration, including having an inwardly chamfered or beveled wall portion 53 to mate with the semi-spherical configuration 51 of the first end 50. Further, to assist in allowing the mating first and second ends 50, 52 of adjacent arm segments 18 to "lock" together and remain fixed in the desired configuration as required by the user in the use position without slipping, the surfaces at the first end 50 and/or second end 52 may have a surface roughness to help prevent any slip between the components when the tightening mechanism 24 of the surgical instrument support 10 is tightened. In one embodiment the roughened surface may be due to a carbide impregnation or via a coarse coating with a hardened material. In addition to varying surface roughness characteristics the different surfaces of the mating surfaces at the first and second ends 50, 52 may have varying surface hardness. In one embodiment the hardness of one of the surfaces has a surface hardness that is greater than surface hardness of the other surface. Preferably, the chamfered or bevel surface 53 of the second end 52 of the arm segments 18 is roughened and has a greater surface hardness than the surface of the first end 50. Further, in addition to having a softer surface hardness the spherical surface 51 of the first end 50 is smoother, or at least not as rough, as the chamfered surface 53 of the second end 52. This configuration has been determined to provide decreased slip between the components.

The end arm segment 20 is positioned adjacent the final arm segment 18 distal the mounting clamp 16. As the first end 44 of the wire 22 is connected to the spindle 38, the second end 46 of the wire 22 is generally connected to the end arm segment 20 to allow all of the arm segments 18 and 20 to be tightened in place as desired against the frame 26 of the mounting clamp 16.

In various embodiments the end arm segment 20 is made up of several individually removable components to provide for increased ease of use and reconfiguring of the surgical instrument support 10 for having different surgical instruments 14 connected thereto. For example, different surgical instruments 14 may require different end arm segments 20 to support those specific surgical instruments 14.

In a preferred embodiment, as shown in FIGS. 3 and 4, the end arm segment 20 is made of three components, an instrument connector member 54, a retainer 56 for retaining the wire 22 and a collar 58. The collar 58 has a flange 60 with an external threaded member 62 extending therefrom. Additionally, the collar 58 has a bore 64 to allow the wire 22 to pass through and to assist in seating a portion of the retainer 56. Similar to the other arm segments 18, the collar 58 of the end arm segment 20 has an end 66 with an inwardly chamfered or beveled wall portion 53 to mate with the semi-spherical configuration 51 of the first end 50 of an adjacent arm segment 18. Like the chamfered portions described above, this portion may also have an roughened surface with an increased surface hardness.

The retainer 56 of the end arm segment 20 has a first portion 68 and a second portion 70. The first portion 68 of the retainer 56 has a smaller diameter than the diameter of the second portion 70 of the retainer 56 to allow the first portion 68 to be seated in the bore 64 of the collar 58. More specifically, the first portion 68 of the retainer 56 can be inserted into the bore 64 of the collar 58 and a shoulder 72 at the joint between the first portion 68 and the second portion 70 of the retainer 56 mates with the end of the collar 58 and operates as a stop to properly seat the retainer 56 in the collar 58.

The retainer 56 also has a bore 74 therethrough to allow the wire 22 to pass through the retainer 56. The bore 74 of the retainer 56, however, has a first opening 76 and a second opening 78, with a shoulder 80 joining the first and second openings 76, 78. The first opening 76 has a larger diameter than the second opening 78 to allow the enlarged portion 45 at the end of the wire 22 to be fitted in the first opening 76 and retained at the shoulder 80 between the first and second openings 76, 78.

The retainer 56 also has a longitudinal slot 82 in its side wall that allows the wire 22 to be inserted into the retainer 56 from the side. When the wire 22 is inserted through the slot 82 and into the bore 74 the enlarged portion 45 at the end of the wire 22 is able to be fixedly seated in the first opening 76 of the bore 74 to fix the second end 46 of the wire 22 in place with respect to the end arm segment 20. Accordingly, the arm component (i.e., including the end arm segment 20, wire 22, arm segments 18, spindle 38 and spring) of the surgical instrument support 10 is a self contained subassembly that can be assembled separately and connected to the mounting clamp 16.

After the wire 22 is secured in the retainer 56, the first portion 68 of the retainer 56, with the wire 22 therein, is inserted into the bore 64 of the collar 58. Next, the connector member 54 can be connected to the collar 58. Specifically, the connector member 54 has an internal threaded opening 84 which mates with the threaded member 62 of the collar 58 to secure the connector member 54 thereto.

The connector member 54 also has a securing member or connector 86 to secure the surgical instrument 12 to the connector member 54 of the surgical instrument support 10. In the embodiment of FIGS. 2 and 3 the surgical instrument 14 is a port. It is understood by those of ordinary skill in the art, however, that the surgical instrument 14 may comprise any instrument, and is not limited in any manner to the port shown in FIGS. 2 and 3. Because different surgical instruments may be needed during surgery, and because different surgical instruments may require different mounting, different connector members 54 may be utilized separately and connected independently to the collar 58 of the end arm member 20.

Further, in the embodiment of FIGS. 5 and 6, the end arm segment 20 has a central bore 90, and a cavity 92 extending through a wall of the end arm segment 20 to provide access to the central bore 90. The end arm segment 20 also has a slot in the wall that allows the user to insert the enlarged portion 45 at the second end 46 of the wire 22 into the central bore 90 and against the cross-sectional portion of the wall (thereby fixing the second end 46 of the wire 22 in place with respect to the end arm segment 20), and the adjacent portion of the wire 22 in the slot and through the hollow bore 19 of the remaining arm segments 18.

In a preferred embodiment, each of the components described above, including the spring 40 and the wire 22, are made from rigid materials that are non-magnetic, and preferably from a non-ferrous metal. Most preferably, the components are made from a high strength titanium alloy, such as a titanium zirconium alloy utilizing minor portions of niobium, tantalum, or vanadium or mixtures thereof. Titanium is an inert component and is completely corrosion resistant. It is 100% hypoallergenic and does not react to salt water, sunlight or body chemistry. Further, titanium is much more flexible, stronger, 40% lighter and more durable than stainless steel, currently the standard material utilized with surgical instruments. In one preferred embodiment the titanium alloy includes 35% Zirconium and 10% Nobium, such as Tiadyne 3510. Tiadyne 3510 exhibits a martensitic microstructure at room temperature after being quenched from 850° C. After aging at approximately 450° C. to 550° C., the tensile and yield strengths are increased significantly. Further, the Tiadyne 3510 may be surface hardened by oxidation to a depth that produces a very high wear resistant outer skin. The hardened outer layer is excellent for articulating parts.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. Additionally, the terms "first," "second," "third," and "fourth" as used herein are intended for illustrative purposes only and do not limit the embodiments in any way. Further, the term "plurality" as used herein indicates any number greater than one, either disjunctively or conjunctively, as necessary, up to an infinite number. Additionally, the term "having" as used herein in both the disclosure and claims, is utilized in an open-ended manner.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying Claims.

What is claimed is:

1. An elongated snake arm surgical instrument support for securing surgical instruments in a fixed position in a surgical environment, the surgical instrument support comprising:
   a mounting clamp connectable to a fixed component in the surgical environment;
   an adjustable tightening mechanism adjacent the mounting clamp, the tightening mechanism having a rotatable crank and a moveable spindle;
   a plurality of mating arm segments provided in series, each arm segment having first and second ends and an aperture extending from the first end to the second end thereof, the first end of each arm segment configured to mate with the second end of an adjacent arm segment, wherein the first end of each mating arm segment has a male mating geometry, and the second end of each mating arm segment has a female mating geometry, the female mating geometry of each mating arm segment being adapted to mate with the male mating geometry of an adjacent mating arm segment, wherein one of the first end of each mating arm segment and the second end of each mating arm segment has a surface that has a first surface hardness and is roughened, and wherein the other of the first end of each mating arm segment and the second end of each mating arm segment has a surface that has a second surface hardness, the second surface hardness being less than the first surface hardness;
   an end member, wherein the end member comprises a separate retainer and instrument connector member; and,
   an elongated line having a first end, a second end and a middle portion therebetween, the first end being connected to one of the crank and the spindle, the second end being operably connected to the end member, and the middle portion extending through the plurality of mating arm segments, wherein one of the crank and the spindle is adjustable to tighten the line between the end member and an arm segment adjacent the mounting clamp to rigidly connect the mating arm segments together in a fixed desirable position;
   wherein the line is removably secured to the retainer to retain each of the arm segments on the line, and wherein the retainer is removably secured to the instrument connector member to allow the instrument connector to be removed from the end member without the line releasing the arm segments from the fixed desirable position.

2. The surgical instrument support of claim 1, wherein each of the mounting clamp, the tightening mechanism, the plurality of mating arm segments, the end member, and the elongated line is formed of titanium alloy.

3. The surgical instrument support of claim 1, wherein the line comprises a titanium alloy stranded wire.

4. The surgical instrument support of claim 1, wherein the mounting clamp has a moveable vise to removably secure the mounting clamp to the fixed component.

5. The surgical instrument support of claim 4, further comprising a rotatable handle to adjust the moveable vise.

6. The surgical instrument support of claim 4, wherein the vice includes a secondary vice rotatably engaged to the mounting clamp, the engagement between the secondary vise and the mounting clamp comprising a plurality of mating teeth to secure the mounting clamp in a variety of angular positions.

7. The surgical instrument support of claim 1, wherein the first end of the line is connected to the spindle and wherein the rotatable crank transitions the spindle from an inward position to a laterally outward position to tighten the line.

8. The surgical instrument support of claim 7, wherein the spindle has a threaded portion and a geometric portion, wherein the mounting clamp has a bore dimensioned to matingly receive the geometric portion of the spindle to prevent the spindle from rotating, and wherein the threaded portion of the spindle engages the crank to allow rotation of the crank to cause the spindle to transition laterally.

9. The surgical instrument support of claim 1, wherein the end member further comprises a collar having a bore to seat a portion of the retainer, the collar further having a threaded portion to engage a mating threaded portion on the instrument connector member to removably secure the retainer to the instrument connector member.

10. An elongated snake arm surgical instrument support for securing surgical instruments in a fixed position in a surgical environment, comprising:
    a mounting clamp connectable to a fixed component in the surgical environment;
    an adjustable tightening mechanism adjacent the mounting clamp, the tightening mechanism having a rotatable crank and a non-rotatable spindle;
    a plurality of mating arm segments provided in series, each arm segment having first and second ends and an aperture extending from the first end to the second end thereof, the first end of each arm segment configured to mate with the second end of an adjacent arm segment;
    an elongated line having a first end, a second end and a middle portion therebetween, the first end being connected to the spindle, and the middle portion extending through the arm segments, wherein the spindle is laterally adjustable to tighten the line to rigidly connect the arm segments together in a fixed desirable position;
    an end arm member adjacent a last of the mating arm segments, the end arm member comprising a retainer having a stepped bore to removably secure the line therein, and a collar, the collar having a central bore to seat the retainer therein and a collar end configured to mate with the first end of the last of the mating arm segments; and,
    a connector member removably secured to the collar of the end arm member, the connector having a securing component to removably connect a surgical instrument to the surgical instrument support, wherein the connector member can be removed from the end arm member without the line releasing the arm segments from the fixed desirable position.

11. The surgical instrument support of claim 10, wherein the collar has a first mating member and wherein the connector has a second mating member that matingly engages the first mating member on the collar to removably secure the connector to the collar.

12. The surgical instrument support of claim 11, wherein the first mating member of the collar comprises a threaded member, and wherein the second mating member of the connector comprises another threaded member.

13. The surgical instrument support of claim 10, wherein the retainer has a longitudinal slot in a sidewall thereof to receive the line therethrough.

* * * * *